(12) United States Patent
Mertes et al.

(10) Patent No.: US 6,392,001 B1
(45) Date of Patent: May 21, 2002

(54) PROCESS FOR THE PRODUCTION OF LIGHT-STABLE POLYISOCYANATES CONTAINING ALLOPHANATE GROUPS

(75) Inventors: Harald Mertes; Josef Pedain, both of Köln; Reinhard Halpaap, Odenthal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/432,285

(22) Filed: May 1, 1995

(30) Foreign Application Priority Data

May 9, 1994 (DE) .......................................... 44 16 321

(51) Int. Cl.$^7$ ............................................. C08G 18/10
(52) U.S. Cl. .................. 528/59; 528/58; 252/182.2; 252/182.21; 252/182.22; 560/25; 560/26; 560/27; 560/115; 560/132; 560/158; 560/159
(58) Field of Search .................... 252/182.2, 182.21, 252/182.22; 528/58, 59; 560/24, 25, 26, 27, 115, 132, 158, 159

(56) References Cited

U.S. PATENT DOCUMENTS

| | | | |
|---|---|---|---|
| 3,769,318 A | 10/1973 | Windemuth et al. | 560/24 |
| 4,160,080 A | 7/1979 | König et al. | 528/59 |
| 4,177,342 A | 12/1979 | Bock et al. | 528/45 |
| 4,738,991 A | 4/1988 | Narayan | 521/124 |
| 4,810,820 A | 3/1989 | Slack et al. | 560/27 |

FOREIGN PATENT DOCUMENTS

| | | |
|---|---|---|
| EP | 016355 | 2/1980 |
| EP | 000016 | 7/1980 |
| EP | 031650 | 7/1981 |
| EP | 393903 | 4/1990 |
| GB | 994890 | 6/1965 |

OTHER PUBLICATIONS

G. Oertel; Polyurethane Handbook; New York; 1985, p. 81.*

Chemical Abstracts, vol. 100 No. 12, Mar. 19, 1984, Abstract No. 86239c, Z. Wirpsza et al.

'Urea amidation of compounds having active hydrogen atoms. Urea amidation of polyethylene glycols.' & Przem. Chem Bd. 62, Nr. 12, 1983, Seiten 679–81.

* cited by examiner

*Primary Examiner*—Rachel Gorr
(74) *Attorney, Agent, or Firm*—Joseph C. Gil; Thomas W. Roy

(57) ABSTRACT

The present invention relates to a process for the production of polyisocyanates containing allophanate groups and having aliphatically and/or cycloaliphatically bound isocyanate groups by reacting organic compounds containing urethane groups with organic polyisocyanates containing aliphatically and/or cycloaliphatically bound isocyanate groups in the presence of tin compounds and to the use of these polyisocyanates, optionally blocked with blocking agents for isocyanate groups, as an isocyanate component in the production of polyurethanes, in particular polyurethane coatings.

8 Claims, No Drawings

PROCESS FOR THE PRODUCTION OF LIGHT-STABLE POLYISOCYANATES CONTAINING ALLOPHANATE GROUPS

BACKGROUND OF THE INVENTION

1. Field of the Invention

This invention relates to a new process for the production of light-colored, light-stable (cyclo)aliphatic allophanate polyisocyanates and to the use of the polyisocyanates obtained by this process as a synthesis component for the production of polyurethanes.

2. Description of the Prior Art

Processes for the production of polyisocyanates containing allophanate groups are described in GB-PS 994,890, U.S. Pat. No. 3,769,318, EP-B 0,000,016, EP-B 0,000,194 and EP-A-0,303,150.

According to GB-PS 994,890, polyisocyanates containing urethane groups are obtained by reacting simple monohydric or polyhydric alcohols with organic polyisocyanates, more particularly diisocyanates, by heating for several hours at elevated temperatures respectively in the presence of catalysts, such as metal carboxylates, metal chelates or tertiary amines. These urethane polyisocyanates are then reacted with further quantities of organic polyisocyanates, preferably diisocyanates, until the isocyanate content calculated for complete reaction of the urethane groups has been reached. According to the British patent, the exact constitution of the reaction products cannot be stated with any certainty. It is concluded from the measured NCO contents of the reaction mixtures or rather the end products isolated therefrom that the reaction products are essentially allophanate polyisocyanates.

As shown in a Comparison Example, strongly colored products are obtained when the reaction is carried out purely thermally in accordance with GB-PS 994,890. According to $^{13}$C-NMR spectroscopy, the products obtained contain not only allophanate polyisocyanates, but also considerable quantities of uretdione, urea and biuret polyisocyanates (which are formed by secondary reactions such as dimerization and biuretization), and also unreacted urethanes. This can be explained by the fact that, when the reaction is terminated at the NCO content calculated for complete allophanatization, one urethane group remains behind unreacted in the reaction mixture for every NCO group reacted off by secondary reaction.

The catalysts described in GB-PS 994,890, such as metal carboxylates, metal chelates and tertiary amines, have long been known as dimerization and/or trimerization catalysts for isocyanates, so that the occurrence of such secondary reactions to a considerable extent during the reaction of urethane groups with isocyanates to form allophanates, as shown in Comparison Examples 3 and 4, is entirely understandable. It is not apparent from the patent specification what conditions and/or catalysts are necessary to produce pure allophanate polyisocyanates. Nor is it apparent what conditions are necessary to obtain light-colored, light-stable products.

The problem of producing allophanate polyisocyanates which are not accompanied by dimeric or trimeric polyisocyanates is addressed in U.S. Pat. No. 3,769,318. According to this patent, allophanate polyisocyanates containing at least one aromatically bound isocyanate group are prepared by reaction of N-substituted carbamic acid esters with isocyanates in the presence of alkylating sulfuric acid or sulfonic acid esters. According to one particular variant, this process is carried out in the presence of certain metal compounds. In the long list of such compounds, the specification mentions, inter alia, tin(II) octoate, although this salt is not used in any of the examples. Accordingly, there is nothing in this prior publication to suggest that the tin compounds according to the present invention described hereinafter should be selected from the long list of suitable metal compounds for the production of purely (cyclo) aliphatic allophanate polyisocyanates.

EP-B 0,000,016 and EP-A 0,303,150 describe the purely thermal reaction of urethanes with organic polyisocyanates to form allophanate polyisocyanates. As can be seen from Comparison Example 1, however, purely thermal reactions of urethanes and isocyanates lead to a considerable extent to secondary reactions and to discoloration of the products.

EP-B 0,000,194 describes a process for the production of allophanate polyisocyanates containing aliphatically and/or cycloaliphatically bound isocyanate groups in which compounds containing urethane groups are reacted with polyisocyanates containing aliphatically and/or cycloaliphatically bound isocyanate groups in the presence of strong acids. Although the presence of strong acids, such as hydrogen chloride, largely suppresses secondary reactions, such as trimerization and biuretization, the products obtained are discolored and tend to darken in color during prolonged storage (Comparison Example 2).

Accordingly, the cited prior art does not suggest how high-quality and, in particular, light-stable, (cyclo)aliphatic allophanate polyisocyanates could be obtained. However, since such polyisocyanates would be expected to be valuable starting materials for the production of light-stable polyurethane lacquers, an object of the present invention is to provide a process for the production of such allophanate polyisocyanates.

Surprisingly, this object may be achieved by carrying out the reaction between aliphatic or cycloaliphatic polyisocyanates and compounds containing urethane groups in the presence of certain tin compounds described in detail hereinafter. The products obtained by the process according to the invention are distinguished by a low color value, high light stability and color stability and, in addition, by comparatively low viscosity. They are also valuable starting materials for the production of polyurethanes, in particular polyurethane coatings.

SUMMARY OF THE INVENTION

The present invention relates to a process for the production of polyisocyanates containing allophanate groups and having aliphatically and/or cycloaliphatically bound isocyanate groups by reacting organic compounds containing urethane groups with organic polyisocyanates containing aliphatically and/or cycloaliphatically bound isocyanate groups in the presence of tin compounds.

The present invention also relates to the use of these polyisocyanates as a synthesis component for the production of polyurethane, more particularly as a crosslinking resin, which may optionally be blocked, for two-component polyurethane lacquers.

DETAILED DESCRIPTION OF THE INVENTION

Starting materials for the process according to the invention are (i) organic compounds containing urethane groups and (ii) organic polyisocyanates containing aliphatically and/or cycloaliphatically bound isocyanate groups.

The compounds containing urethane groups to be used in the process according to the invention are any optionally isocyanate-containing compounds which contain from 1 to 70% by weight and preferably from 1 to 40% by weight of urethane groups (expressed as $CHNO_2$, molecular weight 59) and which, apart from the urethane groups, preferably contain no other H-active, isocyanate-reactive groups. The compounds containing urethane groups may optionally contain isocyanate groups. Suitable compounds include urethane-containing compounds which have been obtained by the reaction of amines containing primary amino groups with chloroformic acid esters. However, the compounds containing urethane groups are preferably reaction products of isocyanates, more particularly polyisocyanates, with organic hydroxyl compounds, i.e. alcohols or phenols, preferably alcohols.

In a preferred embodiment of the process according to the invention the urethane starting materials are prepared in situ from phenols or alcohols and excess quantities of aliphatic or cycloaliphatic polyisocyanates. The reaction mixture obtained in this reaction contains the second main component of the process according to the invention, i.e., the aliphatic or cycloaliphatic polyisocyanate, which was used in excess in the preparation of the urethane.

Preferred compounds containing urethane groups to be used as starting materials in the process according to the invention include those corresponding to the general formula:

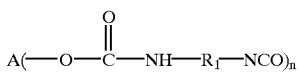

wherein
  A is the residue obtained by the removing the hydroxyl groups from an n-functional organic hydroxyl compound which, apart from the hydroxyl groups, does not contain any other isocyanate-reactive groups,
  $R_1$ represents the residue obtained by removing the isocyanate groups from a diisocyanate containing aliphatically and/or cycloaliphatically bound isocyanate groups and
  n is an integer of 1 to 4, Also suitable are mixtures of urethane-containing compounds corresponding to the above formula with up to 50% by weight, based on the weight of the mixture, of higher homologs of these compounds formed by chain-extending reactions.

The particularly preferred isocyanate-containing urethanes to be used in the process according to the invention generally contain 1 to 40% by weight of urethane groups and 1 to 30% by weight of isocyanate groups, and the substituents A and $R_1$ are (cyclo)aliphatic hydrocarbon radicals.

The isocyanate-containing urethanes corresponding to the above formula are preferably obtained by reacting hydroxyl-containing compounds corresponding to the formula:

with diisocyanates corresponding to the formula:

The reactants are used in quantities corresponding to an NCO:OH equivalent ratio of at least 1.1:1, preferably at least 1.8:1 and, more preferably, of 2:1 to 24:1.

It is also possible, although less preferred to use urethane-containing compounds which have been obtained by reaction of hydroxyl compounds, $A(OH)_n$, with monoisocyanates and/or more than difunctional polyisocyanates, optionally in admixture with diisocyanates, and which optionally contain no free isocyanate groups.

The urethane-containing starting materials required for the process according to the invention are produced by well-known methods of polyurethane chemistry, i.e., in particular by simple heating of the starting materials to 40 to 150° C., preferably to 50 to 100° C. This reaction may optionally be catalyzed by known urethanization catalysts, although it is preferably carried out in the absence of catalysts or by using the catalysts employed for the allophanatization reaction, as described in the following.

Suitable polyhydroxyl compounds $A(OH)_n$ include both phenols (for example, phenol, α-naphthol, cresol, resorcinol or tris-hydroxybenzenes), and preferably alcoholic organic hydroxyl compounds. The preferred alcoholic hydroxyl compounds, $A(OH)_n$, include 1. low molecular weight aliphatic alcohols containing 1 to 4 hydroxyl groups, having a molecular weight of 32 to 250 and optionally; containing ether bridges, such as methanol, ethanol, propanol, isopropanol, allyl alcohol, the isomeric butanols, pentanols, hexanols and heptanols, 2-ethylhexanol, fatty alcohols containing 10 to 20 carbon atoms, ethanediol, propane-1,2- and -1,3-diol, butane 1,2-, -1,3- and -1,4-diol, pentane-1,5-diol, neopentyl glycol, hexane-1,6- and -2,5-diol, 3-methylpentane-1,5-diol, 2-methyl-2-propylpropane-1,3-diol, 2,2diethylpropane-1,3-diol, 2-ethylhexane-1, 3-diol, 2,2,4-trimethylpentane-1,3-diol, trimethylhexane-1,6-diol, decane-1,10-diol, dodecane-1,12-diol, 2-methylbutane-1,4-diol, 2-methylpropane-1,3-diol, glycerol, butanetriol, 2-hydroxymethyl-2-methylpropane-1,3-diol, hexane-1,2,6-triol, trimethylol ethane, trimethylol propane, pentaerythritol, ethylene glycol monoalkyl or monoaryl ether, propylene glycol monoalkyl ether, diethylene glycol, triethylene glycol and tetraethylene glycol.

2. Cycloaliphatic alcohols containing 1 to 4 hydroxyl groups and having a molecular weight of 86 to 250 such as cyclopentanol, cyclohexanol, methyl cyclohexanol, trimethyl cyclohexanol, 4-tert.butyl cyclohexanol, methanol, borneol and isoborneol, 2-hydroxydecalin, 1,2-, 1,3- and 1,4-cyclohexanediol, 2,4-dihydroxy-1,1, 3,3-tetramethyl cyclobutane, 4-bis-(hydroxymethyl)-cyclohexane, bis-(4-hydroxycyclohexyl)-methane, 2,2-bis-(4-hydroxycyclohexyl) -propane, 2,4-bis-(4-hydroxycyclohexyl)-2-methylpentane, furfuryl and tetrahydrofurfuryl alcohol, bis-(hydroxymethyl)-norbornane and bis-(hydroxymethyl)-tricyclodecane.

3. Araliphatic alcohols containing 1 to 4 hydroxyl groups and having a molecular weight of 108 to 300, such as benzyl alcohol, phenyl-ethyl alcohol, 3-phenyl propanol and 4,4'-bis-(2-hydroxyethyl)-diphenyl methane.

4. Polythioethers, polyacetals, polycarbonates or, more particularly, polyesters and polyethers containing 1 to 4 hydroxyl groups and having an average molecular weight of 250 to 5,000, preferably 300 to 2,000.

Suitable polyester polyols include the known reaction products of dihydric and optionally trihydric alcohols (such as those mentioned under 1) with less than equivalent quantities of polybasic, preferably dibasic, carboxylic acids or anhydrides. Examples include adipic acid, phthalic acid, isophthalic acid, phthalic anhydride, tetrahydrophthalic anhydride, hexahydrophthalic anhydride, maleic anhydride and/or dimeric or trimeric oleic acids. Hydroxyl-containing polycaprolactones may also be used as polyester polyols.

Suitable polyether polyols are the known alkoxylation products of suitable starter molecules, for example, the polyhydric alcohols mentioned above under 1, or mixtures of such alcohols. Ethylene oxide and/or propylene oxide are preferably used individually, in admixture and/or sequentially in the alkoxylation reaction.

The aliphatic alcohols mentioned under 1. and the polyester and polyether polyols mentioned under 4. are preferably used in the process according to the invention.

Mixtures of the hydroxyl compounds mentioned above may also be used. It is sometimes a preferred embodiment to use mixtures in the process according to the invention because the functionality of the allophanate polyisocyanate can be varied as required by using hydroxyl compounds of different functionality.

Suitable diisocyanates for use in the production of the urethane-containing compounds used as starting materials in the process according to the invention and as reactants for these urethane-containing compounds correspond to the formula:

$$R_1(NCO)_n$$

wherein
  $R_1$ is an aliphatic hydrocarbon radical containing 2 to 20, preferably 6 to 10 carbon atoms, a cycloaliphatic hydrocarbon radical containing 4 to 20, preferably 6 to 15 carbon atoms or an optionally substituted xylylene radical, Examples of these isocyanates include 1,2-diisocyanatoethane, 1,4-diisocyanatobutane, 1,6-diisocyanatohexane, 1,11-diisocyanatoundecane, 2,2,4- and 2,4,4-trimethyl-1,6-diisocyanatohexane, 1-isocyanato-3-isocyanatomethyl-3,5,5-trimethyl cyclohexane (isophorone diisocyanate), 1,3-diisocyanatocyclobutane, 1,3- and 1,4-diisocyanatocyclohexane, 4,4'-bis-(isocyanatocyclohexyl)-methane, 1,2-bis-(isocyanatomethyl)-cyclobutane, 1,3- and 1,4-bis-(isocyanatomethyl)-cyclohexane, hexahydro-2,4- and/or -2,6-diisocyanatotoluene, bis-isocyanatomethyl norbornane (isomer mixture), 1-isocyanato-4(3)-isocyanatomethyl-1-methyl cyclohexane and p-xylylene diisocyanate. These diisocyanates may be used both in the production of the urethane-containing compounds and as reactants for these compounds. 1,6-diisocyanatohexane and isophorone diisocyanate are particularly preferred.

Monoisocyanates, such as n-hexyl isocyanate or cyclohexyl isocyanate, may also be used in the production of the urethane-containing compounds serving as starting materials, but not as reactants for these compounds in the process according to the invention; however, the use of monoisocyanates is less preferred.

Aliphatic and cycloaliphatic polyisocyanates having a functionality of more than 2 may be also be used both in the production of the urethane-containing compounds serving as starting materials and as; reactants for these compounds. Preferred examples of these polyisocyanates are the isocyanurate-containing trimerization products of 1,6-diisocyanatohexane or isophorone diisocyanate.

Mixtures of isocyanates may be used both in the production of the starting materials containing urethane groups and as reactants for these starting materials, provided that monoisocyanates are not used as reactants for the urethane-containing compounds. The use of monoisocyanates reduces the NCO functionality of the products obtained by the process according to the invention. The functionality of the products obtained by the process according to the invention can be varied through the choice of certain mixing ratios between the isocyanate components and through the choice of the mixing ratio between hydroxyl compounds.

The presence of tin compounds during the reaction of the compounds containing urethane groups with the isocyanate component to form the corresponding allophanates containing isocyanate groups is critical to the invention.

These tin compounds are tin salts and organotin compounds. Preferred tin compounds are tin compounds, which are soluble in the reaction mixture and have a tin content of 10 to 65% by weight, in particular, tin(II) and organotin salts of organic acids and also tin(II) halides. Examples of preferred tin compounds are tin(II) chloride, bromide and iodide, tin(II) octanoate, tin(II) 2-ethylhexanoate and dibutyl tin dilaurate. Tin(II) salts of organic acids, such as tin(II) n-octanoate and tin(II) 2-ethylhexanoate, are particularly preferred.

The tin compounds are used in quantities of 0.001 to 5.0% by weight, preferably 0.01 to 1.0% by weight, based on the total weight of the reactants, in the process according to the invention.

The tin compounds may be incorporated in the reaction mixture by any suitable method. For example, the tin compound may be mixed with the hydroxyl compound before the preparation of the compound containing urethane groups. In cases where a two-stage process is used, the tin compound may also be added to the reaction mixture before the preparation of the allophanate compounds.

To carry out the process according to the invention, the reactants are generally used in such quantities that there are 2 to 50, preferably 3 to 12, isocyanate groups of the polyisocyanate component for every urethane group of the compound containing urethane groups. Accordingly, where the compound containing urethane groups is prepared in situ, a corresponding excess of the isocyanate component is used.

The reaction according to the invention generally takes place at temperatures of 50 to 140° C. The course of the reaction according to the invention may be followed by determining the NCO content of the reaction mixture. The reaction may be terminated at any time, for example, by cooling to room temperature.

In a preferred embodiment of the process according to the invention the starting compound containing urethane groups is prepared in situ. In this process a diisocyanate, which is preferably used as the isocyanate component, is initially introduced at 50 to 80° C. and the hydroxyl component is added dropwise in liquid form with thorough stirring. If the same isocyanate or isocyanate mixture is to be used both for urethanization and for allophanatization, it is initially used in an amount such that the NCO/OH equivalent ratio is 3:1 to 12:1.

On completion of the urethane reaction (monitored by determining the NCO content), the temperature is increased to 80 to 140° C. and the catalyst (the tin compound) is added. The reaction mixture is stirred until the NCO content has fallen to the value calculated for complete allophanatization. The tin catalyst may also be initially introduced together with the isocyanate or added together with the hydroxyl compound.

If the polyisocyanate containing allophanate groups is to be freed from excess diisocyanate, this may be done either by thin-layer distillation or by fractional extraction, for example, using n-hexane or cyclohexane as extractant.

The type of starting materials used and the quantities in which they are used in the process according to the invention are generally selected so that allophanates containing at least two isocyanate groups, i.e. allophanate polyisocyanates, are formed. These products are distinguished by excellent stability during the thin-layer treatment, even at temperatures of 180° C. and higher. The secondary and equilibrium reactions observed in the production of uretdione or biuret polyisocyanates, which lead to troublesome caking and to an increase in viscosity, do not take place.

The process according to the invention may be carried out continuously by arranging several reactors in tandem in the form of a cascade. Diisocyanate, hydroxyl compound and catalyst are continuously introduced into the first reactor. Adjustment of the temperature and the throughput ensures that the reaction is complete on leaving the last reactor. The crude product then passes through a thin-layer evaporator where it is freed from excess diisocyanate which is returned to the first reactor.

The end products of the process according to the invention are distinguished by a low color value, high light stability and color stability and by comparatively low viscosity.

The excellent stability in storage of the allophanate polyisocyanates according to the invention freed from excess starting isocyanate is particularly emphasized. The end products of the process according to the invention do not have any tendency to eliminate monomeric starting isocyanate and, in this respect, advantageously differ in particular from known uretdione or biuret polyisocyanates.

The products obtained from the process according to the invention are valuable starting materials for the production of polyurethanes by the isocyanate polyaddition process, more particularly for the production of one-component or two-component polyurethane coatings. When these products are blocked with known blocking agents for isocyanate groups, they are also particularly suitable for the production of polyurethane stoving lacquers.

Preferred reactants for the optionally blocked polyisocyanates according to the invention to produce polyurethane coatings are the polyhydroxy polyesters, polyhydroxy polyacrylates and optionally low molecular weight polyhydric alcohols known in polyurethane lacquer technology. Suitable reactants of this type are described, for example, in DE-AS 2,304,893.

The quantities in which the optionally blocked polyisocyanates according to the invention and the reactants mentioned are reacted to produce polyurethane coatings are selected such that, for every (optionally blocked) isocyanate group, there are 0.8 to 3, preferably 0.9 to 1.1 hydroxyl, amino, mercapto and/or carboxyl groups.

The curing process may be accelerated by using known catalysts, e.g., tertiary amines, such as triethylamine, pyridine, methyl pyridine, benzyl dimethylamine, N,N-dimethyl cyclohexylamine, N-methyl piperidine, pentamethyl diethylenetriamine, N,N'-endoethylene piperazine and N,N'-dimethyl piperazine; and metal salts, such as iron(III) chloride, zinc chloride, zinc 2-ethylhexanoate, tin(II) 2-ethylhexanoate, dibutyl tin dilaurate and molybdenum glycolate.

The allophanate polyisocyanates may also be used in one-component coating compositions. High-quality gloss coatings are obtained by curing with atmospheric moisture. Less than equivalent quantities of OH components, preferably the OH-functional reactants already mentioned, may optionally be used. They are used in such a quantity that, for every OH group, there are at least 1.25 and preferably 1.5 to 10 NCO groups. The catalysts mentioned may also be used for one-component coating compositions.

When the allophanate polyisocyanates are used in stoving lacquers, the NCO groups are completely or partly blocked in known manner. The polyisocyanate is reacted with a suitable blocking agent, preferably at elevated temperature (for example 40 to 140° C.), optionally in the presence of a suitable catalyst, e.g., tertiary amines and metal salts, such as zinc 2-ethylhexanoate, tin(II) 2-ethylhexanoate, dibutyl tin dilaurate or alkali metal phenolate.

Suitable blocking agents include monophenols, such as phenol, the cresols, the trimethylphenols and the tert.butylphenols; tertiary alcohols, such as tert.butanol, tert.amyl alcohol and dimethylphenyl carbinol; compounds which readily form enols, such as acetoacetic ester, acetyl acetone and malonic acid derivatives (such as malonic acid diesters containing 1 to 8 carbon atoms in the alcohol components); secondary aromatic amines, such as N-methyl aniline, the N-methyl toluidines, N-phenyl toluidine and N-phenyl xylidine; imides, such as succinimide; lactams, such as c-caprolactam and δ-valerolactam; oximes, such as butanone oxime and cyclohexanone oxime; mercaptans, such as methyl mercaptan, ethyl mercaptan, butyl mercaptan, 2-mercaptobenzthiazole, α-naphthyl mercaptan and dodecyl mercaptan.

The coating compositions according to the invention, in addition to the previously described optionally blocked polyisocyanates, poly-functional reactants and catalyst, may optionally contain known additives such as pigments, dyes, fillers and flow control agents. The components are thoroughly mixed together and homogenized in a standard mixing unit, for example a dissolver, in the presence or absence of solvents and diluents.

The lacquers and coating compositions may be applied to the substrate to be coated in solventless, liquid form, in solution, from the melt or in solid form by standard methods such as spread coating, roll coating, casting, spray coating, fluidization dip coating or electrostatic powder spraying.

The coating compositions containing the polyisocyanates according to the invention provide films which adhere surprisingly well to metallic substrates, are particularly light-stable, color-stable on exposure to heat and highly abrasion-resistant and, providing they are used in air-drying lacquers, dry particularly quickly, even at temperatures around 0° C. They are also distinguished by considerable hardness, elasticity, very high resistance to chemicals, high gloss, excellent weathering resistance and good pigmentability.

The invention is illustrated by the following examples in which all parts and percentages are by weight unless otherwise indicated.

EXAMPLES

Example 1

74 g (1 mole) of n-butanol were added dropwise at 70° C. to 336 g (2 moles) of 1,6-diisocyanatohexane (HDI), followed by stirring for 1 hour until an NCO content of the reaction mixture of 30.7% (which corresponds to complete urethanization) was obtained. After the temperature had been increased to 100° C., 0.1 g (0.02%, based on the reaction mixture) of tin(II) 2-ethylhexanoate were added. The reaction mixture was then stirred for 2 h at 100° C. until the NCO content was 20.5%, which corresponded to complete allophanatization. The isocyanate structures in the reaction mixture were quantitatively determined by $^{13}$C-NMR spectroscopy (see Table 1). The reaction mixture was then subjected to thin-layer distillation resulting in 334 g (81.4%) of a product having an NCO content of 12.9%, a viscosity of 890 mPa.s at 23° C. and a Hazen color value of 20.

Comparison Example 1
(catalyst-free according to GB-PS 994,890)

336 g (2 moles) of HDI and 74 g (1 mole) of n-butanol were stirred at 70° C. until the NCO content of the reaction mixture was 30.7% (complete urethanization). The temperature was then increased to 150° C. and the reaction mixture was stirred at that temperature for 24 h until the NCO content of the reaction mixture was 22.3%, which corresponded to substantial allophanatization. The isocyanate structures were quantitatively determined by $^{13}$C-NMR spectroscopy (see Table 1). Since the reaction mixture was bright yellow in color, it was not subjected to working up by distillation.

Comparison Example 2
(hydrogen chloride as catalyst according to EP-B 0,000,194)

336 g (2 moles) of HDI and 74 g (1 mole) of n-butanol were reacted at 70° C. to form the urethane (NCO content 30.7%). After the temperature had been increased to 100° C., 4.1 g (1%) of hydrogen chloride were added (in the form of an 8% solution of hydrogen chloride in HDI, i.e., formation of carbamoyl chloride). The reaction mixture was then stirred for 5 h at 100° C. until the NCO content was 20.5%, which corresponded to complete allophanatization. The reaction mixture was analyzed by $^{13}$C-NMR spectroscopy (Table 1) and worked up by thin-layer distillation. 332 g (81%) of a pale yellow product having an NCO content of 12.9%, a viscosity of 930 mPa.s at 23° C. and a Hazen color value of 50 were obtained. After storage for 2 weeks, the Hazen color value was 150 units.

TABLE 1

$^{13}$C-NMR spectroscopic analysis

| | | Comparison Example | |
|---|---|---|---|
| Structure [% by weight] | Example 1 | 1 | 2 |
| Urethane | — | 19.2 | 10.5 |
| Allophanate | 97.8 | 65.0 | 82.4 |
| Uretdione | — | 3.3 | 1.6 |
| Isocyanurate | 2.2 | — | 1.6 |
| Urea | — | 6.2 | 1.0 |
| Biuret | — | 6.3 | 3.0 |

$^{13}$C-NMR-spectroscopic analyses were carried out using a Bruker AMX-500 spectrometer at 125.76 MHz with proton noise decoupling (PND). Dimethylsulfoxide-$d_6$ was used as solvent and $^2$H "lock"; tetramethyl silane (TMS) was the internal standard. The structures were assigned on the basis of the carbonyl C atom signals at 148 to 160 ppm (against TMS). The molar quantities obtained therefrom were converted into % by weight.

Example 2

In a 2 liter three-necked flask, 75 g (0.5 mole) of triethylene glycol were added dropwise over a period of 30 minutes at 70° C. to 1008 g (6 moles) of 1,6-diisocyanatohexane (HDI). After another 30 minutes at 70° C., the NCO content of the reaction mixture was 42.7%, which corresponded to complete reaction of the OH groups to urethane groups. After the temperature had been increased to 100° C., 0.3 g (0.03%) of tin(II) 2-ethylhexanoate was added. After 3 hours at 100° C., the NCO content of the reaction mixture was 38.8%, which corresponded to complete reaction of the urethane groups to allophanate groups. The crude product was subjected to thin-layer distillation. 422 g of a substantially colorless product (Hazen color value 25) having a viscosity of 1300 mPas at 23° C. and an NCO content of 18.8% were obtained. The product was analyzed for its composition by gel permeation chromatography (GPC) and the results are set forth in Table 2.

Comparison Example 3
(according to GB-PS 994,890, zinc naphthenate as catalyst as in Example 5)

1008 g (6 moles) of 1,6-diisocyanatohexane (HDI) and 75 g (0.5 mole) of triethylene glycol were reacted as in Example 2 until urethanization was complete (NCO content 42.7%). 1.15 g of zinc naphthenate were then added. The NCO content fell to 38.8% over a period of 8 hours at 50° C. Working up by thin-layer distillation gave a brown-yellow product having an NCO content of 20.4% and a viscosity at 25° C. of 1350 mPa.s.

For GPC analysis, see Table 2.

Comparison Example 4
(according to GB-PS 994,890, tertiary amine as catalyst as in Example 4)

As in Comparison Example 3, the urethane solution was prepared and stirred for 24 h at 70° C. after addition of 1.15 g of diazabicyclooctane. However, the theoretical reduction in the NCO content was only achieved after another 16 h at 120° C. Working up gave a deep yellow oil having a viscosity of 1050 mPas at 25° C. and an NCO content of 20.2%.

For GPC analysis, see Table 2.

TABLE 2

GPC analysis

| Component [percentage per unit area] | Example 2 | Comparison Example 3 | Comparison Example 4 |
|---|---|---|---|
| HDI | 0.2 | 0.7 | 0.5 |
| Dimeric diisocyanate | 0.5 | 1.5 | 6.3 |
| Trimeric diisocyanate | 2.9 | 10.6 | 11.3 |
| Bis-urethane of 1 mole triethylene glycol and 2 moles diisocyanate | 1.0 | 10.3 | 10.3 |
| Monourethane monoallophanate of 1 mole triethylene glycol and 3 moles diisocyanate | 1.6 | 9.8 | 15.6 |
| Bis-allophanate of 1 mole triethylene glycol and 4 moles diisocyanate | 31.9 | 20.8 | 12.2 |
| Sum total of all polymer homologs | 61.9 | 46.3 | 43.8 |

Examples 3–13

Examples 3–13 were conducted following the procedure of Example 1 using the materials and conditions set forth in Tables 3 and 4 to obtain products having the characteristics also set forth in these tables.

TABLE 3

| | Examples 3–8 | | | | | |
|---|---|---|---|---|---|---|
| Example | 3 | 4 | 5 | 6 | 7 | 8 |
| Isocyanate | HDI | HDI | HDI | HDI | HDI | HDI |
| Alcohol | n-BuOH | n-BuOH | n-BuOH | n-BuOH | n-BuOH | n-BuOH |
| NCO/OH | 4.0 | 6.0 | 8.0 | 10.0 | 4.0 | 10.0 |
| Catalyst | A | A | A | A | B | B |
| [%] | 0.04 | 0.02 | 0.02 | 0.02 | 0.05 | 0.05 |

TABLE 3-continued

Examples 3–8

| Example | 3 | 4 | 5 | 6 | 7 | 8 |
|---|---|---|---|---|---|---|
| Reaction temperature [° C.] | 110 | 110 | 110 | 110 | 110 | 110 |
| Reaction time [h] | 2 | 3 | 2 | 1.5 | 4 | 1.5 |
| $NCO_{end}$ [%] | 20.3 | 29.1 | 33.8 | 36.7 | 20.8 | 36.6 |
| $Yield_{resin}$ [%] | 80.7 | 58.9 | 46.0 | 38.9 | 76.9 | 39.2 |
| $NCO_{resin}$ [%] | 12.7 | 15.3 | 17.4 | 18.6 | 12.5 | 17.8 |
| Viscosity [mPa · s] | 870 | 200 | 160 | 140 | 1050 | 240 |
| Hazen color value | 25 | 25 | 30 | 25 | 40 | 40 |

Catalyst:
A = tin(II) 2-ethylhexanoate
B = tin(II) chloride

TABLE 4

Examples 9–13

| Example | 9 | 10 | 11 | 12 | 13 |
|---|---|---|---|---|---|
| Isocyanate | HDI | HDI | IPDI | IPDI | IPDI |
| Alcohol | MeOH | EtOH | n-BuOH | n-BuOH | n-BuOH |
| NCO/OH | 8.0 | 8.0 | 6.0 | 8.0 | 10.0 |
| Catalyst | A | A | A | A | A |
| [%] | 0.05 | 0.05 | 0.1 | 0.1 | 0.1 |
| Reaction temperature [° C.] | 110 | 110 | 110 | 110 | 110 |
| Reaction time [h] | 2 | 2,5 | 5 | 3,5 | 3 |
| $NCO_{end}$ [%] | 34.9 | 35.0 | 23.1 | 26.2 | 28.0 |
| $Yield_{resin}$ [%] | 48.1 | 47.2 | 56.8 | 41.9 | 38.0 |
| $NCO_{resin}$ [%] | 18.6 | 18.4 | 13.4 | 13.8 | 14.2 |
| Viscosity [mPa · s] | 540 | 270 | 230* | 200* | 180* |
| Hazen color value | 30 | 30 | 50 | 40 | 50 |

*= 70% solution in methoxypropyl acetate
Catalyst:
A = tin(ii) 2-ethylhexanoate
B = tin(ii) chloride Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate containing allophanate groups and in which the isocyanate groups consist essentially of aliphatically and/or cycloaliphatically bound isocyanate groups which comprises reacting an organic compound containing urethane groups with an organic polyisocyanate containing aliphatically and/or cycloaliphatically bound isocyanate groups in the presence of a tin compound.

2. The process of claim 1 wherein said tin compound is soluble in the reaction mixture, has a tin content of 10 to 65% by weight and is present in a quantity of 0.001 to 5% by weight, based on the total weight of the reactants.

3. The process of claim 1 wherein said tin compound is a tin(II) salt of an organic acid.

4. The process of claim 2 wherein said tin compound is a tin(II) salt of an organic acid.

5. A coating composition comprising an isocyanate-reactive component and the polyisocyanate prepared in accordance with claim 1.

6. A two-component coating composition containing an isocyanate-reactive component and the polyisocyanate in accordance with claim 1.

7. The process of claim 1 wherein said tin compound is a tin(II) halide.

8. The process of claim 2 wherein said tin compound is a tin(II) halide.

* * * * *